(12) United States Patent
Wijesundara et al.

(10) Patent No.: US 11,172,731 B2
(45) Date of Patent: Nov. 16, 2021

(54) DUAL-LAYER INSOLE APPARATUSES FOR DIABETIC FOOT LESION PREVENTION AND RELATED METHODS

(71) Applicants: THE BOARD OF REGENTS OF THE UNIVERSITY OF TEXAS SYSTEM, Austin, TX (US); THE UNIVERSITY OF NORTH TEXAS HEALTH SCIENCE CENTER AT FORT WORTH, Fort Worth, TX (US)

(72) Inventors: Muthu B. J. Wijesundara, Austin, TX (US); Wei Carrigan, Austin, TX (US); Ryan Landrith, Austin, TX (US); Metin Yavuz, Fort Worth, TX (US)

(73) Assignees: The Board of Regents of the Universsity of Texas Systems, Austin, TX (US); The University of North Texas Health Science Center At Fort Worth, Fort Worth, TX (US)

( * ) Notice: Subject to any disclaimer, the term of this patent is extended or adjusted under 35 U.S.C. 154(b) by 35 days.

(21) Appl. No.: 16/464,443

(22) PCT Filed: Nov. 28, 2017

(86) PCT No.: PCT/US2017/063400
§ 371 (c)(1),
(2) Date: May 28, 2019

(87) PCT Pub. No.: WO2018/098463
PCT Pub. Date: May 31, 2018

(65) Prior Publication Data
US 2019/0373984 A1    Dec. 12, 2019

Related U.S. Application Data

(60) Provisional application No. 62/426,896, filed on Nov. 28, 2016.

(51) Int. Cl.
A43B 17/03       (2006.01)
A43B 7/14        (2006.01)
(Continued)

(52) U.S. Cl.
CPC .......... *A43B 17/035* (2013.01); *A43B 3/0005* (2013.01); *A43B 7/144* (2013.01);
(Continued)

(58) Field of Classification Search
None
See application file for complete search history.

(56) References Cited

U.S. PATENT DOCUMENTS 3,283,799 A    11/1966 Barbera
3,538,628 A    11/1970 Einstein
(Continued)

FOREIGN PATENT DOCUMENTS

KR    2007/0090474    9/2007
WO    WO/15/191007   12/2015
(Continued)

OTHER PUBLICATIONS

Aubin et al., "A pediatric robotic thumb exoskeleton for at-home rehabilitation : The isolated orthosis for thumb actuation (IOTA)"., International Journal of Intelligent Computing and Cybernetics 7(3), 2014.
(Continued)

*Primary Examiner* — Jila M Mohandesi
(74) *Attorney, Agent, or Firm* — Meunier Carlin & Curfman LLC

(57) ABSTRACT

Dual-layer insole apparatuses for diabetic foot lesion prevention and related methods are provided. Some insole apparatuses have a body defining a plurality of cavities configured to be coupled to a fluid source. The fluid source
(Continued)

can deliver fluid to vary internal pressures of the cavities. The body further defines an insole-shaped structure.

20 Claims, 14 Drawing Sheets

(51) Int. Cl.
| A43B 5/14 | (2006.01) |
| A43B 13/20 | (2006.01) |
| A43B 3/00 | (2006.01) |
| A61F 5/14 | (2006.01) |
| A43B 17/02 | (2006.01) |

(52) U.S. Cl.
CPC ............ *A43B 7/147* (2013.01); *A43B 7/1445* (2013.01); *A43B 7/1475* (2013.01); *A43B 13/203* (2013.01); *A43B 13/206* (2013.01); *A61F 5/14* (2013.01); *A43B 17/026* (2013.01)

(56) References Cited

U.S. PATENT DOCUMENTS

| 3,574,386 | A | | 4/1971 | Frost |
| 3,834,046 | A | | 9/1974 | Fowler |
| 3,922,801 | A | * | 12/1975 | Zente ...................... A43B 13/20 36/44 |
| 4,183,156 | A | * | 1/1980 | Rudy .................... A43B 17/035 36/29 |
| 4,471,538 | A | * | 9/1984 | Pomeranz ............ A43B 13/189 188/322.5 |
| 5,156,629 | A | | 10/1992 | Shane et al. |
| 5,158,767 | A | * | 10/1992 | Cohen ................... A43B 5/0407 36/114 |
| 5,237,501 | A | | 8/1993 | Gusakov |
| 5,267,365 | A | | 12/1993 | Walter |
| 5,423,094 | A | | 6/1995 | Arsenault et al. |
| 5,771,606 | A | * | 6/1998 | Litchfield ............ A43B 13/203 36/28 |
| 5,813,142 | A | * | 9/1998 | Demon ................ A43B 3/0005 36/28 |
| 5,878,510 | A | * | 3/1999 | Schoesler ............. A43B 7/147 36/43 |
| 5,881,407 | A | | 3/1999 | Chu Pt |
| 5,916,664 | A | | 6/1999 | Rudy |
| 6,014,823 | A | * | 1/2000 | Lakic ............... A41D 19/01523 36/11.5 |
| 6,092,249 | A | | 7/2000 | Kamen et al. |
| 6,463,612 | B1 | * | 10/2002 | Potter .................... A43B 13/20 12/146 B |
| 6,510,624 | B1 | * | 1/2003 | Lakic ................... A43B 5/0407 36/28 |
| 6,560,803 | B2 | | 5/2003 | Zur |
| 7,555,848 | B2 | * | 7/2009 | Aveni ..................... A43B 13/20 36/29 |
| 8,127,373 | B1 | | 3/2012 | Fodemski |
| 8,523,794 | B2 | | 9/2013 | Iker et al. |
| 9,119,439 | B2 | * | 9/2015 | Brandt .................. B29C 51/267 |
| 9,839,260 | B1 | * | 12/2017 | Chang .................... A43B 17/14 |
| 2001/0018564 | A1 | * | 8/2001 | Manor ................. A61H 1/0266 601/152 |
| 2002/0004120 | A1 | | 1/2002 | Hillier |
| 2002/0128572 | A1 | | 9/2002 | Chang |
| 2003/0009913 | A1 | | 1/2003 | Potter et al. |
| 2003/0131417 | A1 | | 7/2003 | Roux |
| 2003/0181990 | A1 | | 9/2003 | Phillips |
| 2004/0083550 | A1 | | 5/2004 | Graebe |
| 2005/0043585 | A1 | | 2/2005 | Datta et al. |
| 2006/0085919 | A1 | | 4/2006 | Kramer et al. |
| 2006/0174518 | A1 | | 8/2006 | Fogarty et al. |
| 2006/0248749 | A1 | * | 11/2006 | Ellis ..................... A43B 13/181 36/28 |
| 2008/0097263 | A1 | * | 4/2008 | Grigoriev ................ A43B 7/00 601/151 |
| 2009/0000037 | A1 | | 1/2009 | Graebe |
| 2011/0163885 | A1 | | 7/2011 | Poulos et al. |
| 2012/0054965 | A1 | | 3/2012 | Kummer et al. |
| 2014/0013514 | A1 | | 1/2014 | Misaki |
| 2014/0026327 | A1 | | 1/2014 | Taylor |
| 2014/0167460 | A1 | | 6/2014 | Prexl et al. |
| 2015/0335167 | A1 | | 11/2015 | Cinquin |
| 2016/0252110 | A1 | | 9/2016 | Galloway et al. |
| 2017/0086588 | A1 | | 3/2017 | Zouzal et al. |

FOREIGN PATENT DOCUMENTS

| WO | WO-2016191190 A1 * | 12/2016 | ........... A43B 7/1445 |
| WO | WO-2017095945 A1 * | 6/2017 | ........... A43C 11/165 |

OTHER PUBLICATIONS

Balasubramanian et al., "Robot-assisted rehabilitation of hand function" Curr. Opin. Neurol. 23(6), 2010. Available: http://journals.lww.com/co-neurology/Fulltext/2010/12000/Robot_assisted_rehabilitation_of_hand_function.19.aspx.

Birch et al., "Design of a continuous passive and active motion device for hand rehabilitation", Presented at Engineering in Medicine and Biology Society, 2008. EMBS 2008. 30th Annual International Conference of the IEEE. 2008,. DOI 10.1109/IEMBS.2008.4650162.

Board, et al. "A comparison of trans-tibial amputee suction and vacuum socket conditions." *Prosthetics and Orthotics International*, 25(3);202-209, 2001.

Brand, "Tenderizing the Foot," *Foot & Ankle International*, 24(6); 457-461, 2003.

Bus, et al., "The Effectiveness of Footwear and Offloading Interventions to Prevent and Heal Foot Ulcers and Reduce Plantar Pressure in Diabetes: A Systematic Review," *Diabetes Metabolism Research & Reviews*, 24 (SI); 99-118, 2008.

Chantelau, et al., "How Effective is Cushioned Therapeutic Footwear in Protecting Diabetic Feet? A Clinical Study," *Diabetic Medicine*, 7(4); 355-359, 1990.

Connelly et al., "A pneumatic glove and immersive virtual reality environment for hand rehabilitative training after stroke" Neural Systems and Rehabilitation Engineering, IEEE Transactions On 18(5), pp. 551-559, 2010, DOI 10.1109/TNSRE.2010.2047588.

Convery & Buis, "Conventional Patellar-Tendon-Bearing (PTB) Socket/Stump Interface Dynamic Pressure Distributions Recorded During the Prosthetic Stance Phase of Gait of a Trans-Tibial Amputee," *Prosthetics and Orthotics International*, 22(3); 193-198, 1998.

Dargis, et al., "Benefits of a Multidisciplinary Approach in the Management of Recurrent Diabetic Foot Ulceration in Lithuania: A Prospective Study," *Diabetes Care*, 22(9); 1428-1431, 1999.

Edmonds, et al., "Improved Survival of the Diabetic Foot: The Role of a Specialized Foot Clinic," *Quarterly Journal of Medicine*, 60(232); 763-771, 1986.

Faudzi, et al., "Design and Control of New Intelligent Pneumatic Cylinder for Intelligent Chair Tool Application," 2009 IEEE/IAS International Conference on Advanced Intelligent Mechatronics, Singapore, 1909-1914, 2009.

Hagberg & Branemark, "Consequences of Non-Vascular Trans-Femoral Amputation: A Survey of Quality of Life, Prosthetic Use and Problems." *Prosthetics and Orthotics International*, 25(3); 186-194, 2001.

Haghshenas-Jaryani M, Carrigan W, Wijesundara MBJ: "Design and Development of a Novel Soft-and-Rigid Actuator System for Robotic Applications", Paper No. 47761, Proceedings of the ASME 2015 International Design Engineering Technical Conferences & Computers and Information in Engineering Conference IDETC/CIE2015 Aug. 2-5, 2015, Boston, MA, USA.

Hamanami, et al., "Finding the Optimal Setting of Inflated Air Pressure for a Multi-Cell Air Cushion for Wheelchair Persons with Spinal Cord Injury," *Acta Medica Okayama*, 58(1): 37-44, 2004.

Heo and Kim, "Power-assistive finger exoskeleton with a palmar opening at the fingerpad" Biomedical Engineering, IEEE Transactions On 61(11), pp. 2688-2697. 2014. . DOI: 10.1109/TBME.2014.2325948.

(56) References Cited

OTHER PUBLICATIONS

Ho, et al., "An EMG-driven exoskeleton hand robotic training device on chronic stroke subjects: Task training system for stroke rehabilitation" Presented at Rehabilitation Robotics (ICORR), 2011 IEEE International Conference On. 2011, . DOI: 10.1109/ICORR.2011.5975340.

Hume et al., "Functional range of motion of the joints of the hand," J.Hand Surg., vol. 15, No. 2, March pp. 240-243, 1990.

International Preliminary Report on Patentability in International Application No. PCT/US2014/072338 dated Jun. 28, 2016.

International Preliminary Report on Patentability Issued In Corresponding PCT Application No. PCT/US2018/028599, dated Oct. 22, 2019.

International Preliminary Report on Patentability Issued in Corresponding PCT Application No. PCT/US2017/064218, dated Jun. 4, 2019.

International Preliminary Report on Patentability Issued in Corresponding PCT Application. No. PCT/US2017/063400, dated May 28, 2019.

International Search Report and Written Opinion in International Application No. PCT/US2014/072338 dated Jun. 2, 2015.

International Search Report and Written Opinion Issued in Corresponding PCT Application No. PCT/US2017/064218, dated Mar. 28, 2018.

International Search Report and Written Opinion Issued in Corresponding PCT Application No. PCT/US2017/063400, dated Feb. 9, 2018.

International Search Report and Written Opinion Issued in Corresponding PCT Application No. PCT/US2018/28599, dated Aug. 1, 2018.

Kadowaki et al., "Development of Soft Power-Assist Glove and Control Based on Human Intent," Journal of Robotics and Mechatronics, vol. 23, No. 2, pp. 281-291, 2011.

Kawasaki et al., "Development of a hand motion assist robot for rehabilitation therapy by patient self-motion control" Presented at Rehabilitation Robotics, 2007. ICORR 2007. IEEE 10$^{th}$ International Conference On. 2007,. DOI: 10.1109/ICORR.2007.4428432.

Lavery, et al., "Shear-Reducing Insoles to Prevent Foot Ulceration in High-Risk Diabetic Patients," *Advances in Skin & Wound Care*, 25(11); 519-524, 2012.

Loureiro and Harwin. "Reach & grasp therapy: Design and control of a 9-DOF robotic neurorehabilitation system" Presented at Rehabilitation Robotics, 2007. ICORR 2007. IEEE 10th International Conference On. 2007,. DOI: 10.1109/ICORR.2007.4428510.

Lum et al., "Robotic approaches for rehabilitation of hand function after stroke" American Journal of Physical Medicine & Rehabilitation 91(11), 2012. Available: http://dx.doi.org/10.1097/PHM.0b013e31826bcedb. DOI: 10.1097/PHM.0b013e31826bcedb.

Polygerinos et al., "Soft robotic glove for combined assistance and at-home rehabilitation", Robotics and Autonomous Systems, 73; 135-143, 2015.

Polygerinos et al., "Towards a soft pneumatic glove for hand rehabilitation" Presented at Intelligent Robots and Systems (IROS), 2013 IEEE/RSJ International Conference On. 2013, . DOI: 10.1109/IROS.2013.6696549.

Reiber, et al., "Effect of Therapeutic Footwear on Foot Reulceration in Patients with Diabetes: A Randomized Controlled Trial," *The Journal of the American Medical Association*, 287(19); 2552-2558, 2002.

Sanders, et al., "Clinical Utility of In-Socket Residual Limb Volume Change Measurement: Case Study Results," *Prosthetics and Orthotics International*, 33(4); 378-390, 2009.

Schabowsky et al., "Development and pilot testing of HEXORR: Hand EXOskeleton rehabilitation robot" Journal of NeuroEngineering and Rehabilitation 7(1), p. 36. 2010. Available: http://www.jneuroengrehab.com/content/7/1/36.

Uccioli, et al., "Manufactured Shoes in the Prevention of Diabetic Foot Ulcers," *Diabetes Care*, 18(10); 1376-1378, 1995.

Ueki et al., "Development of a Hand-Assist Robot With Multi-Degrees-of-Freedom for Rehabilitation Therapy," Mechatronics, IEEE/ASME Transactions on, vol. 17, No. 1, pp. 136-146, 2012.

Ueki et al., "Development of virtual reality exercise of hand motion assist robot for rehabilitation therapy by patient self-motion control" Presented at Engineering in Medicine and Biology Society, 2008. EMBS 2008. 30th Annual International Conference of the IEEE. 2008, . DOI: 10.1109/IEMBS.2008.4650156.

Vermeulen, et al., "Trajectory Planning for the Walking Biped Lucy," *The International Journal of Robotics Research*, 25(9): 867-887, 2006.

Wege & Hommel, "Development and control of a hand exoskeleton for rehabilitation of hand injuries" Human Interaction with Machines, G. Hommel and S. Huanye, Eds. 2006, 149-157, DOI: 10.1007/1-4020-4043-1_16.

* cited by examiner

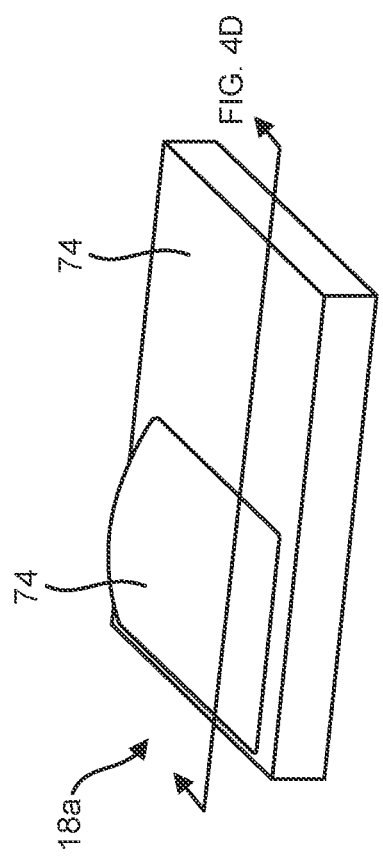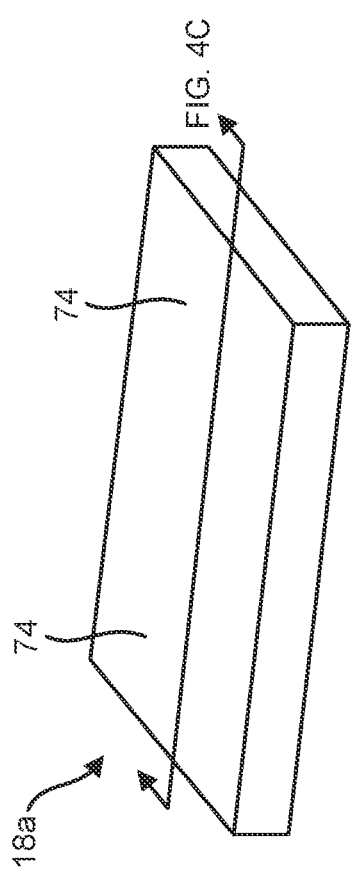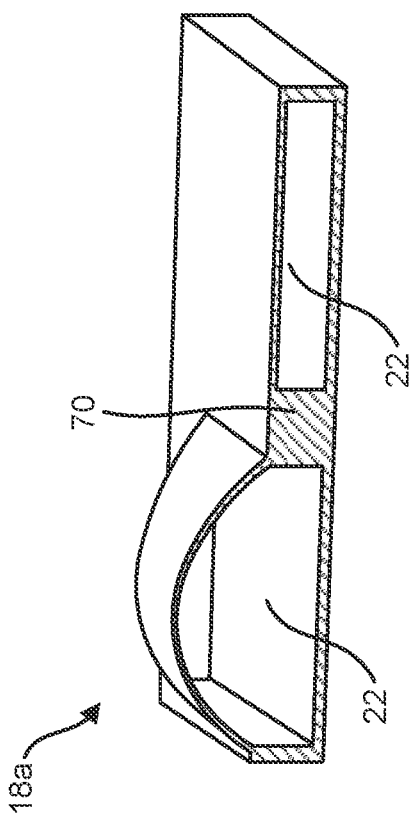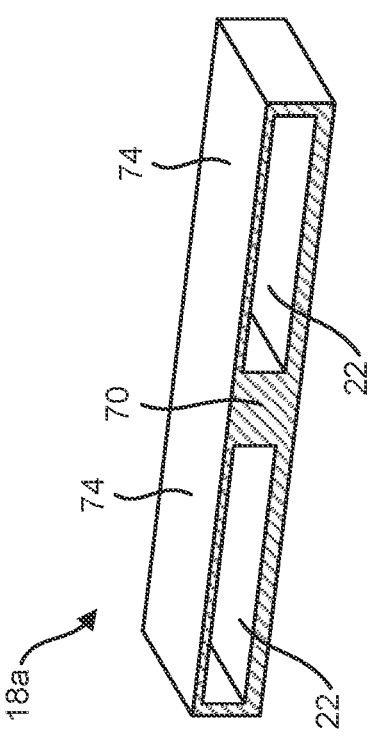

DUAL-LAYER INSOLE APPARATUSES FOR DIABETIC FOOT LESION PREVENTION AND RELATED METHODS

CROSS-REFERENCE TO RELATED APPLICATION

This application is a national phase application under 35 U.S.C. § 371 of International Application No. PCT/US2017/063400, filed Nov. 28, 2017 which claims the benefit of priority to U.S. Provisional Patent Application No. 62/426,896 filed Nov. 28, 2016. All applications listed in this paragraph are hereby incorporated in their respective entireties.

BACKGROUND

1. Field of Invention

The present invention relates generally to insole apparatuses, and more specifically, but not by way of limitation, to dual-layer insole apparatuses for diabetic foot lesion prevention and related methods.

2. Description of Related Art

Foot lesions, and more particularly, foot ulcers, have long been associated with elevated plantar pressures and shear stresses in diabetic patients. Prolonged mechanical stresses and cyclic mechanical loading in diabetic patients with peripheral neuropathy are contributing causes of some diabetic ulcers. Studies have suggested that current footwear designed to prevent diabetic foot ulcers has been less effective than previously anticipated.

The lifetime risk of developing a foot ulcer for diabetic patients is in the range of 15-25 percent. Diabetic foot ulcers continue to burden the U.S. healthcare system with an annual cost of approximately $30 billion. Nearly 100,000 amputations are performed yearly, burdening the quality of lives of diabetic patients. The fact that the 5-year mortality rate of diabetic patients with a foot ulcer is comparable with that of some cancer patients, suggests that approximately half of these individuals will be deceased within 5 years. Since prevention is the most effective treatment, efforts to prevent diabetic foot ulcers before they occur may be an crucial way to avoid the costs and social burden caused by ulcers and related amputations.

Diabetic foot ulcers often have a multifactorial pathology. Thus, preventive devices that address only one factor at a time may not effectively prevent ulcer development. Several footwear designs have been implemented to reduce peak pressure in diabetic patients, yet the prevention of foot lesions is only partially successful at best, and marginal in many cases. Edmonds et al. observed ulceration rates of 26% in patients wearing specially designed footwear. See Edmonds, M. E., et al., *Improved survival of the diabetic foot: the role of a specialized foot clinic*, Quarterly Journal of Medicine, 60(232), 763-771 (1986). Other reports suggest that the ulceration rates can be as high as 28%, 30%, and 42% in studies in patients wearing specially designed footwear. See Uccioli, L., et al., *Manufactured shoes in the prevention of diabetic foot ulcers*, Diabetes Care, 18(10), 1376-1378 (1995), Dargis, V., et al., *Benefits of a multidisciplinary approach in the management of recurrent diabetic foot ulceration in Lithuania: a prospective study*, Diabetes Care, 22(9), 1428-1431 (1999), and Chantelau, E., et al., *How effective is cushioned therapeutic footwear in protecting diabetic feet? A clinical study*, Diabetic Medicine, 7(4), 355-359 (1990). Another study, which investigated the use of therapeutic footwear in 400 subjects, found no significant difference in ulcer prevention rates among the intervention and control groups. See Reiber, G. E., et al., *Effect of therapeutic footwear on foot reulceration in patients with diabetes: a randomized controlled trial*, The Journal of the American Medical Association, 287(19), 2552-2558 (2002). In a systematic review by Bus et al., the effectiveness of pressure-reducing footwear in preventing diabetic ulceration was shown to be inadequate. See Bus, S. A., et al., *The effectiveness of footwear and offloading interventions to prevent and heal foot ulcers and reduce plantar pressure in diabetes: a systematic review*, Diabetes Metabolism Research & Reviews, 24 (S1), S162-S180 (2008). A recent clinical trial that explored the effectiveness of shear-reducing insoles in diabetic ulceration did not report favorable results as well. See Lavery, L. A., et al., *Shear-reducing insoles to prevent foot ulceration in high-risk diabetic patients*, Advances in Skin & Wound Care, 25(11), 519-524 (2012).

One researcher suggested that an individual with normal sensation may unconsciously alter his or her gait to prevent excessive loading in a specific region of the foot, and that diabetic ulcers might occur due to a lack of such selective loading in the presence of neuropathy. See Brand P. W., *Tenderizing the foot*, Foot & Ankle International, 24(6), 457-461 (2003). This suggestion has been further supported by clinical practice for pressure ulcer reduction through prepositioning of immobile patients and the use of alternating mattresses to provide selective rest to different parts of the body, which otherwise become vulnerable due to restricted blood perfusion and prolonged mechanical stress.

SUMMARY

The present apparatuses and methods not only reduce peak pressures (e.g., via body 18) and shear stresses (e.g., via body 62) on a plantar surface of a foot but also provide the capability of regulating cyclic loading to given areas to facilitate the blood perfusion and address prolonged application of repetitive mechanical loading in the foot. The present apparatuses and methods can be utilized to prevent not only diabetic foot ulcers but also metatarsal stress fractures. The present apparatuses and methods can be used in pain relief footwear targeted for individuals with rheumatoid arthritis. The present apparatuses and methods can be integrated into total contact casts and/or other offloading devices (e.g., diabetic boots) to periodically offload the ulcer site and thereby accelerate wound healing. Gradual loading of the ulcer area may also be possible with the present apparatuses and methods, which may contribute to faster tissue regeneration.

Key advantages of the present apparatuses and methods include: reducing localized pressures and/or shear forces through improved fitting strategies and increased load-bearing surface areas, automatic alteration of a patient's gait pattern without the patient's intervention, facilitating blood perfusion in a foot, and reducing prolonged cyclic mechanical loading (e.g., by periodically modulating and/or redistributing pressure and shear forces on a plantar surface of the foot).

Some embodiments of the present insole apparatuses comprise: a body defining a plurality of cavities configured to be coupled to a fluid source such that the fluid source can deliver fluid to vary internal pressures of the cavities; and wherein the body defines an insole-shaped structure.

Some embodiments further comprise a substantially flat substrate configured to be coupled to one or more of the cavities.

In some embodiments, the body is configured to be disposed under a patient's foot such that one or more of the cavities is disposed under a plantar surface of at least one portion of the patient's foot selected from the group consisting of: a metatarsal head, a hallux, and a calcaneus bone.

Some embodiments further comprise a flexible substrate configured to be disposed over the cavities such that the flexible substrate matches the contours of the plurality of cavities. In some embodiments, the flexible substrate includes a plurality of flexible substrate segments, each of which is configured to be disposed over a respective cavity. In some embodiments, the body includes a plurality of protrusions extending toward the flexible substrate to define the cavities. In some embodiments, a first one of the protrusions is separated from second one of the protrusions by a distance between 1 millimeter (mm) and 6 mm. In some embodiments, each of the protrusions includes an elastomeric material configured to deform when the internal pressure of the respective cavity is varied.

Some embodiments further comprise at least one sensor configured to capture data indicative of a pressure in one or more of the cavities.

In some embodiments, the fluid source comprises a pump and a fluid reservoir. In some embodiments, the fluid source comprises one or more features of the group consisting of: a pump, one or more fluid reservoirs, a valve, a pressure regulator, and a pressurized air canister.

Some embodiments further comprise one or more valves configured to direct fluid to one or more of the cavities.

Some embodiments further comprise: a fluid source configured to be coupled to the cavities; and a processor configured to control the fluid source to, while pressure in a first one or more of the cavities remains substantially constant: (a) increase pressure of a second one or more of the cavities; (b) after a predetermined amount of time, decrease pressure of the second one or more of the cavities; and (c) increase pressure of a third one or more of the cavities.

In some embodiments, a first one or more of the cavities is in a first region of the body extending from a first side of the substrate to a second side of the substrate, wherein the first region is closer to a first end of the substrate than a second end of the substrate; a second one or more of the cavities is in a second region of the body extending from the first region toward the first end and along the first side; and a third one or more of the cavities are in a third region of the body extending from the first side to the second side at the second end. In some embodiments, when in use, the first region is configured to be disposed under a plantar surface of one or more metatarsal heads of a foot. In some embodiments, when in use, the second region is configured to be disposed under a plantar surface of a hallux of a foot. In some embodiments, when in use, the third region is configured to be disposed under a plantar surface of a calcaneus bone of a foot.

Some embodiments comprise a second body defining a plurality of cavities configured to be coupled to the fluid source such that the fluid source can deliver fluid to vary internal pressures of the cavities, wherein, when in use, the second body is configured to be positioned above a dorsal surface of a foot.

Some embodiments of the present methods (e.g., for actuating an insole apparatus having a body defining a plurality of cavities configured to be coupled to a fluid source such that the fluid source can deliver fluid to vary internal pressures of the cavities, wherein the body defines an insole-shaped structure) comprise: while pressure in a first one of the cavities remains substantially constant: (1) increasing pressure of a second one of the cavities; (2) after a first predetermined amount of time, decreasing pressure of the second one or more of the cavities; (3) increasing pressure of a third one or more of the cavities; (4) after a second predetermined amount of time, decreasing pressure of the third one or more of the cavities; and (5) increasing pressure of a fourth one or more of the cavities. In some embodiments, steps (1)-(5) are controlled by a processor. Some embodiments comprise repeating steps (1)-(5). Some embodiments comprise simultaneously decreasing pressure of at least two of the first, second, and third one or more of the cavities.

In some embodiments, the second one or more of the cavities is aligned with a plantar surface of one or more metatarsal heads of a foot; the third one or more of the cavities is aligned with the plantar surface of a hallux of the foot; and the fourth one or more of the cavities is aligned with the plantar surface of a calcaneus bone of the foot.

In some embodiments, the pressure in the first, second, and/or third one of the cavities is increased to a value between 0.5 pounds per square inch (psi) and 30 psi.

In some embodiments, the first predetermined amount of time is between 30 seconds to 30 minutes, and/or the second predetermined amount of time is between 30 seconds to 30 minutes.

Some embodiments of the present methods (e.g., for actuating an insole apparatus having a body defining a plurality of cavities configured to be coupled to a fluid source such that the fluid source can deliver fluid to vary internal pressures of the cavities, wherein the body defines an insole-shaped structure) comprise: (1) increasing a first, second, and third one of the cavities to a first pressure; (2) decreasing pressure of the second one of the cavities to a second pressure while maintaining the first and third one of the cavities at the first pressure; (3) after a first predetermined amount of time, increasing pressure of the second one of the cavities to the first pressure; (4) decreasing pressure of the third one of the cavities to the second pressure while maintaining the first and second one of the cavities at the first pressure; (5) after a second predetermined amount of time, increasing pressure of the third one or more of the cavities to the first pressure; and (6) decreasing pressure of the first one of the cavities to the second pressure while maintaining the second and third one of the cavities at the first pressure. In some embodiments, steps (1)-(6) are controlled by a processor. Some embodiments comprise repeating steps (1)-(6). Some embodiments comprise simultaneously decreasing pressure of at least two of the first, second, and third one or more of the cavities.

In some embodiments, the first one or more of the cavities is aligned with a plantar surface of one or more metatarsal heads of a foot; the second one or more of the cavities is aligned with the plantar surface of a hallux of the foot; and the third one or more of the cavities is aligned with the plantar surface of a calcaneus bone of the foot.

In some embodiments, the first pressure and/or the second pressure are between 0.5 pounds per square inch (psi) and 30 psi.

In some embodiments, the first predetermined amount of time is between 30 seconds to 30 minutes, and/or the second predetermined amount of time is between 30 seconds to 30 minutes.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The phrase "and/or" means and or or. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes," one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Further, an apparatus that is configured in a certain way is configured in at least that way, but it can also be configured in other ways than those specifically described.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIGS. 4A and 4B are first and second perspective views of a first embodiment of a body that may be suitable for use in some embodiments of the present apparatuses, shown with a cavity in a first position and a second position, respectively.

FIGS. 4C and 4D are first and second cutaway perspective views of the body of FIGS. 4A and 4B, shown with the cavity in the first position and the second position, respectively.

FIGS. 16A-17C depict pressure modulation data of the apparatus of FIG. 1.

DETAILED DESCRIPTION

Figure 1:
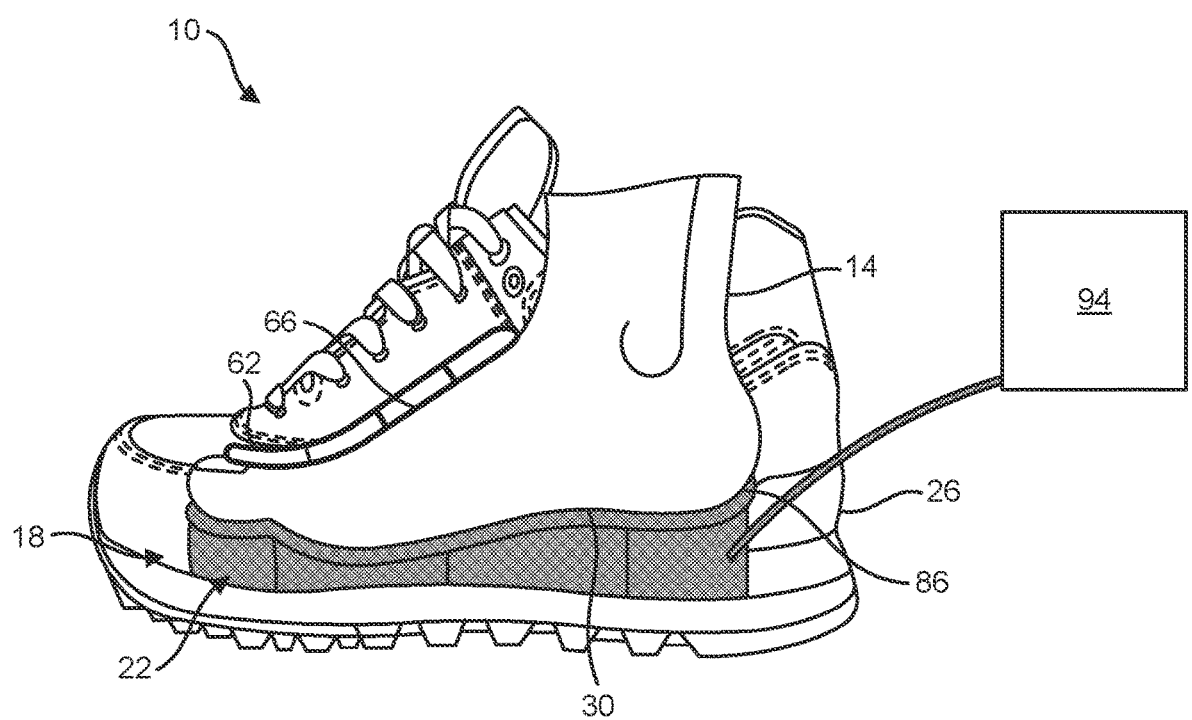
FIG. 1 is a side view of a first embodiment of the present insole apparatuses, shown with a shoe and a control unit.
Figure 2:
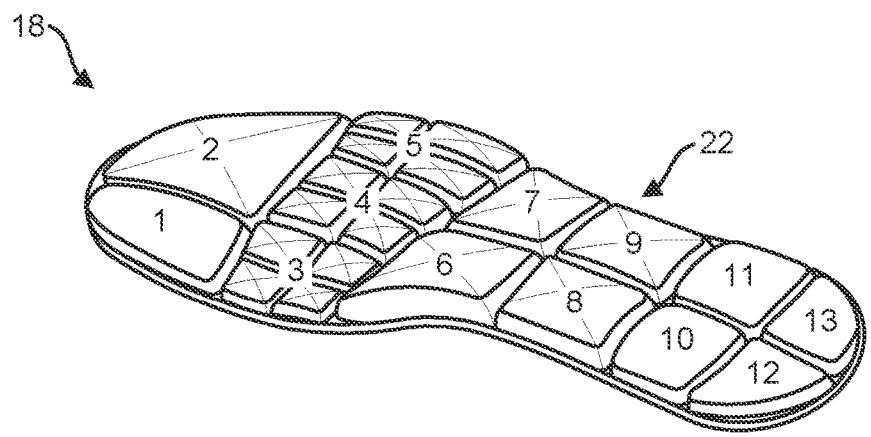
FIGS. 2 and 3 are perspective and top views, respectively, of the insole apparatus of FIG. 1, shown without the shoe and the control unit.
Figure 3:
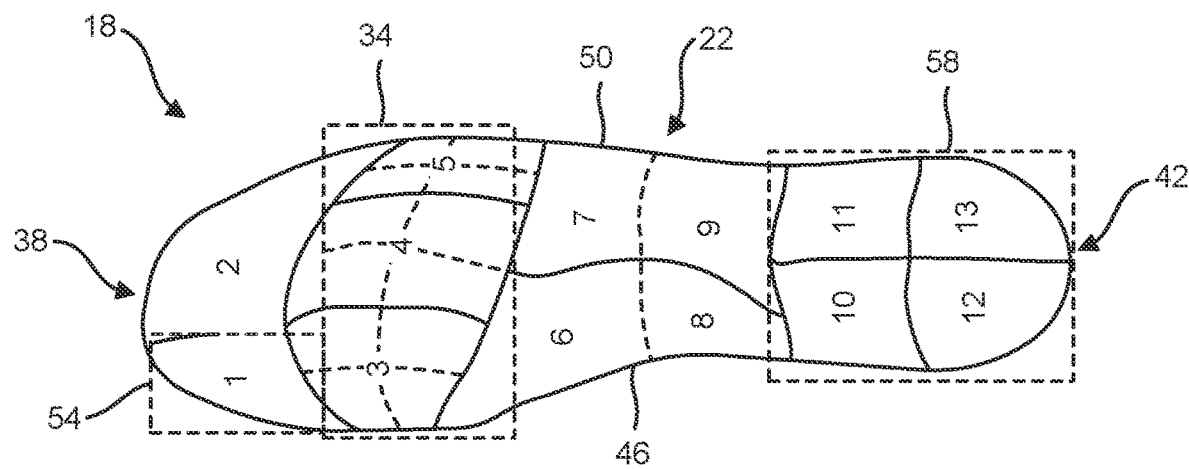
Figure 5B:
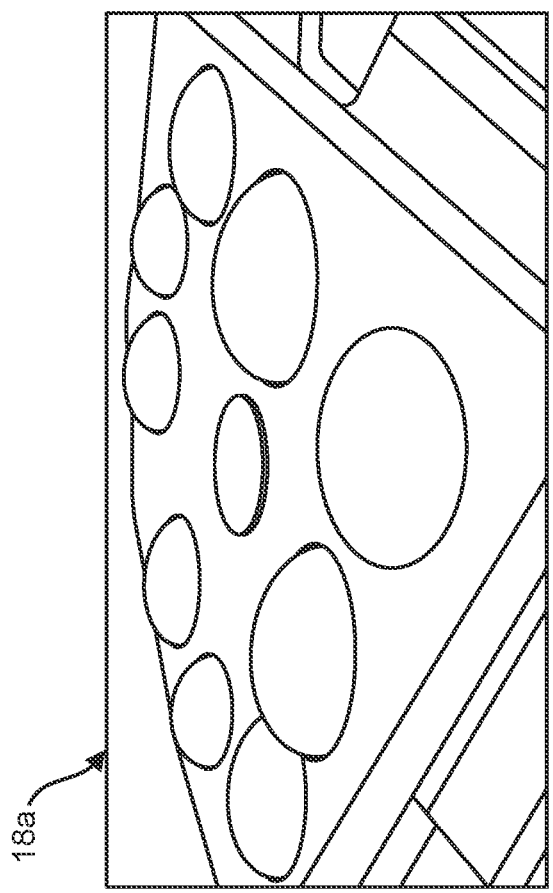
FIGS. 5A and 5B are first and second perspective views of a fabricated unit of the body of FIGS. 4A and 4B, shown with a plurality of cavities in a first position and a second position, respectively.
Figure 5A:
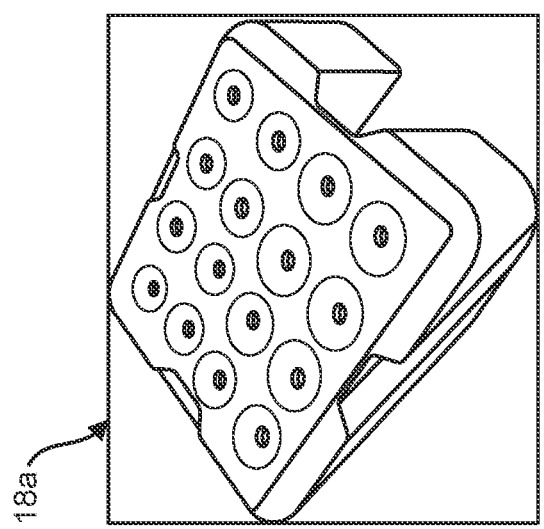
Figure 6B:
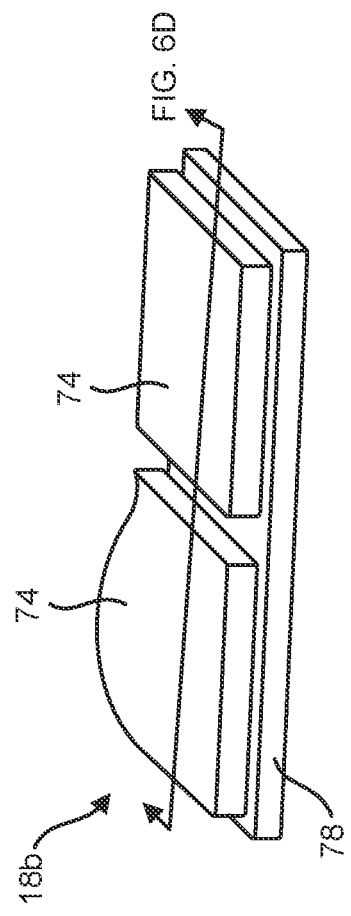
FIGS. 6A and 6B are first and second perspective views of a second embodiment of a body that may be suitable for use in some embodiments of the present apparatuses, shown with a cavity in a first position and a second position, respectively.
Figure 6A:
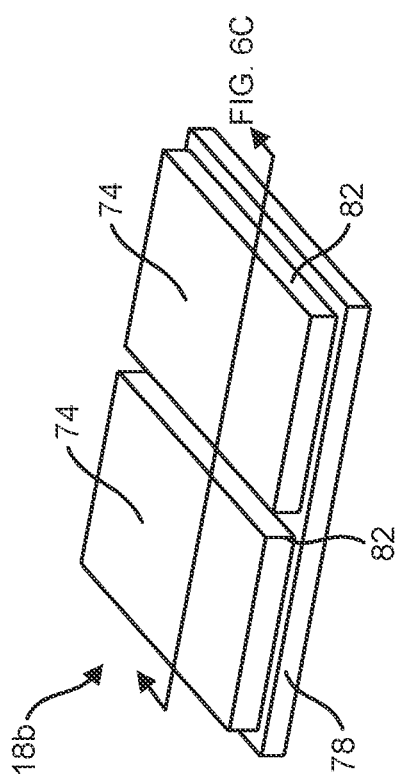
Figure 6D:
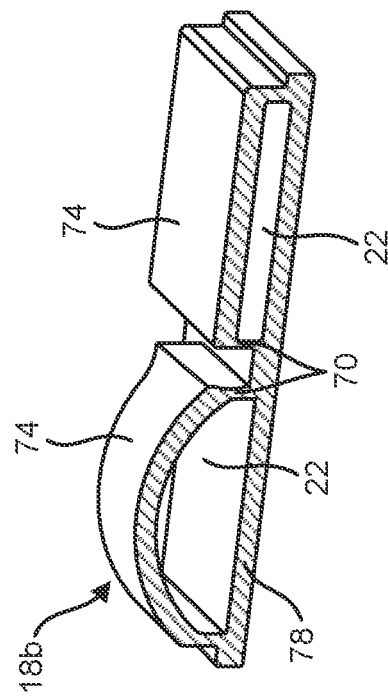
FIGS. 6C and 6D are first and second cutaway perspective views of a portion of the body of FIGS. 6A and 6B, shown with the cavity in the first position and the second position, respectively.
Figure 6C:
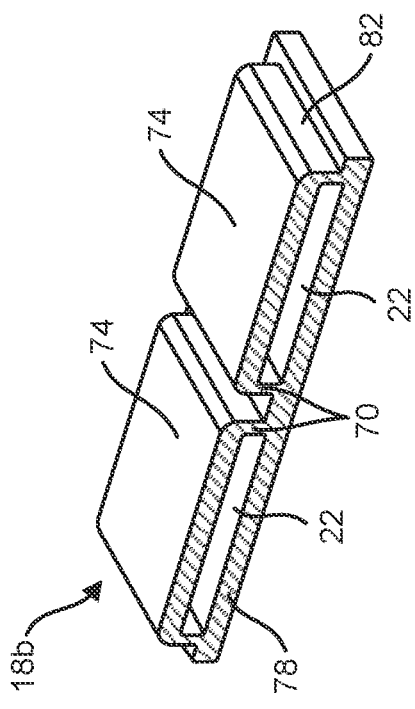
Figure 7:
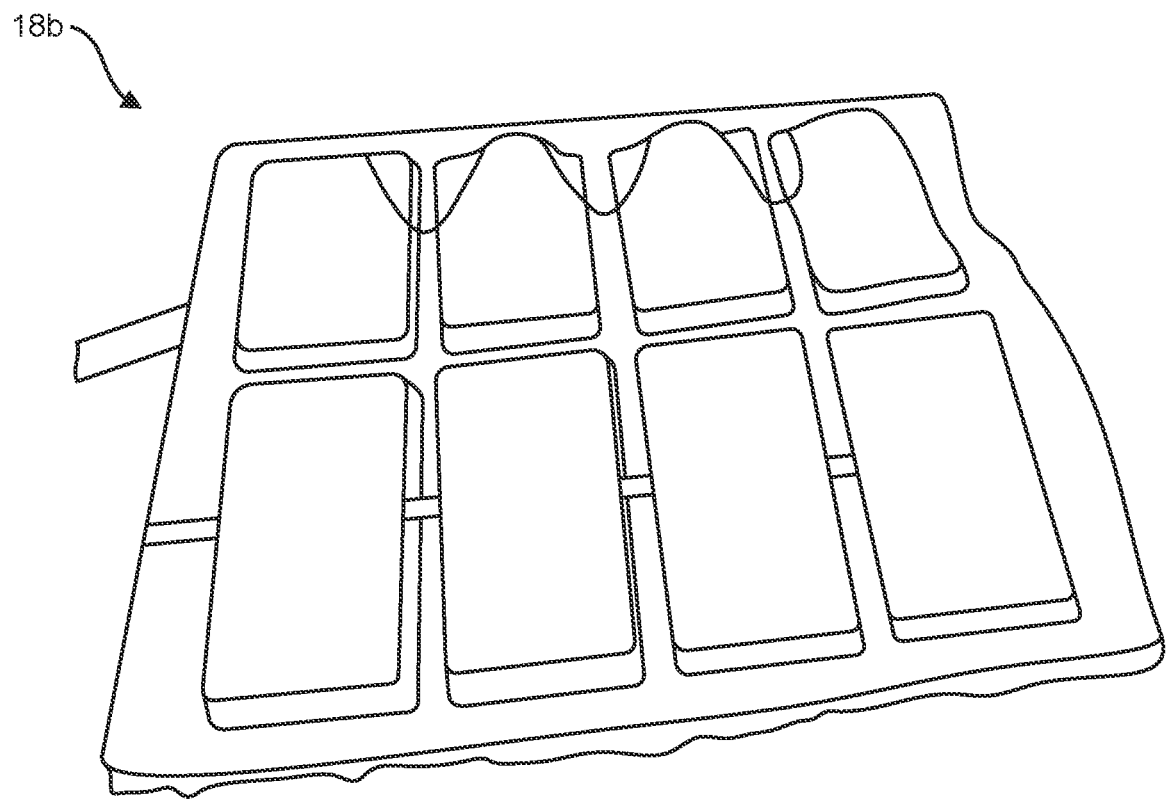
FIG. 7 is a perspective view of a first fabricated unit of the body of FIGS. 6A and 6B, with a plurality of cavities in a first position and a plurality of cavities in a second position, respectively.
Figure 8:
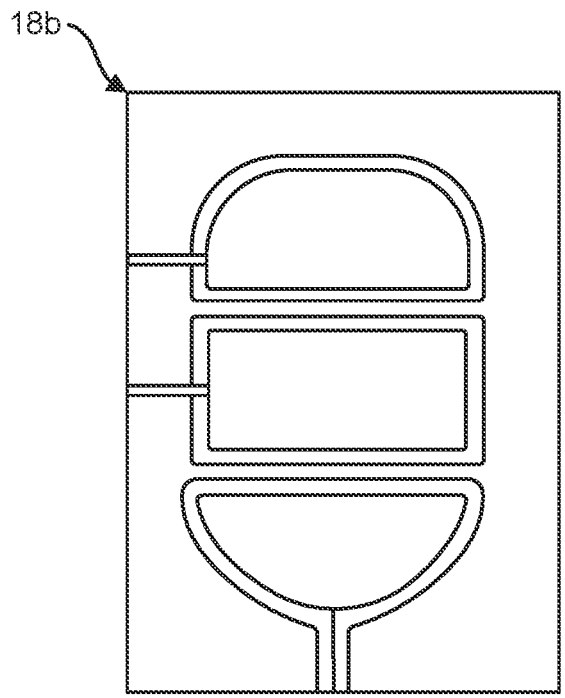
FIGS. 8 and 9 are top views of second and third fabricated units, respectively, of bodies of the type shown in FIGS. 6A and 6B.
Figure 9:
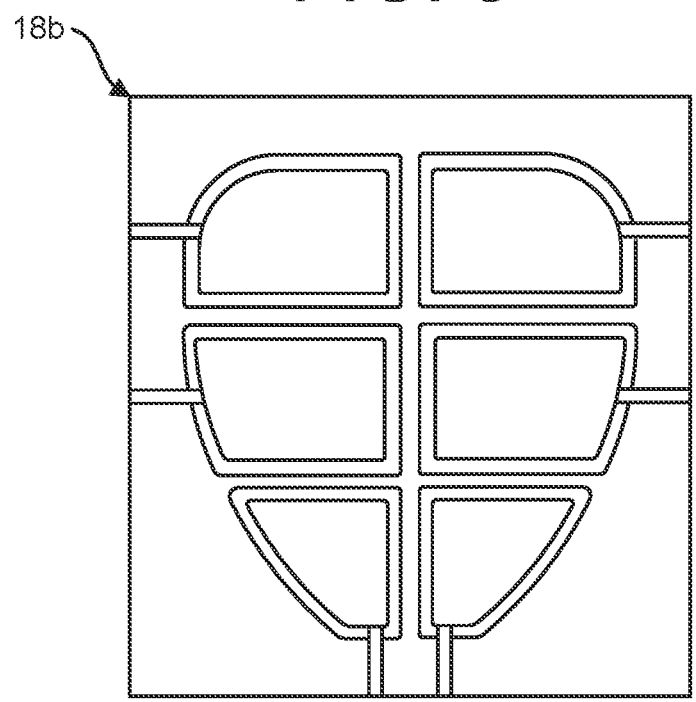
Figure 10:
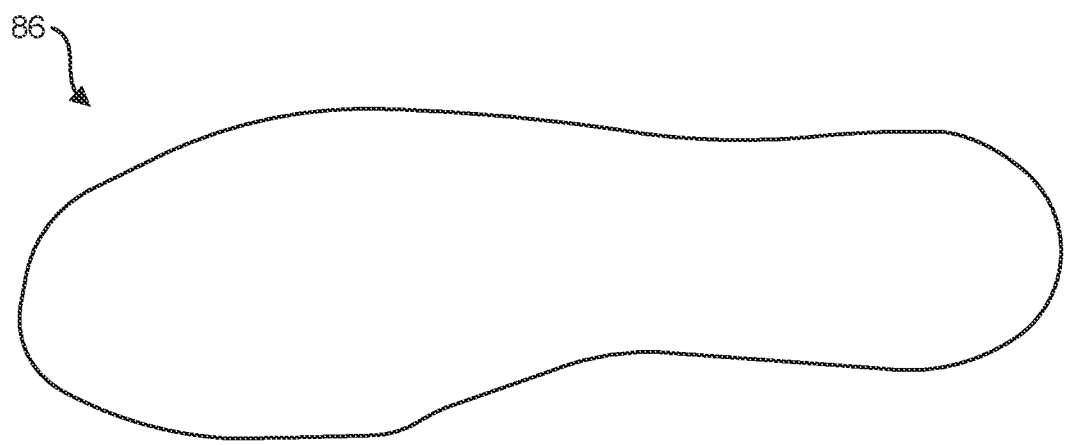
FIG. 10 is a top view of a first embodiment of a substrate that may be suitable for use in some embodiments of the present apparatuses.

FIG. 1 depicts a first embodiment 10 of the present insole apparatuses. Apparatus 10 is configured to periodically modulate and/or distribute pressure and shear stresses on a foot 14 of a patient to prevent lesions, such as, for example, foot ulcers caused by high cyclical mechanical loading (e.g., due to walking, running, and/or the like) and, in at least some instances, exacerbated by peripheral neuropathy. Apparatus 10 includes a body 18 defining a plurality of cavities 22. As shown, body 18 defines an insole-shaped structure configured to fit in a shoe 26.

One or more of cavities 22 can be configured to be modulated by periodically increasing and/or decreasing an internal pressure in the one or more cavities such that apparatus 10 reduces and/or increases mechanical loading on alternating portions of a foot 14. In at least this way, apparatus 10 prevents prolonged exposure to mechanical stresses, which can result in foot ulcers. For example, one or more of cavities 22 can be configured to be coupled to a fluid source (e.g., 102) such that the fluid source can deliver fluid to vary internal pressures of the one or more of the cavities. One or more of cavities 22 can be pressurized to an initial pressure such that, when apparatus 10 is disposed in a shoe 26, the cavities conform to a plantar surface 30 of the foot 14 to conform to the foot of the patient. For example, one or more of cavities 22 can be filled with fluid before fitting (e.g., before a patient puts on a shoe 26) and/or one or more of the other cavities can be filled with fluid after fitting (e.g., while the patient wears on the shoe). In this embodiment, two or more of cavities 22 can be filled with the same fluid. For example, two or more of cavities 22 may be in fluid communication with each other, such as to share fluid therebetween. In other embodiments, two or more of cavities (e.g., 22) may be filled with different fluid. Fluid within one or more of cavities 22 may comprise liquid (e.g., hydraulic fluid), gas (e.g., pneumatic fluid), and/or the like.

Cavities 22 are arranged on body 18 such that the cavities interface with a plantar surface 30 of a foot 14. To illustrate, body 18 is configured to be disposed under a patient's foot 14 such that one or more of cavities 22 is disposed under a plantar surface 30 of at least one portion of the foot selected from the group consisting of: one or more metatarsal heads, a hallux, and a calcaneus bone.

Apparatus 10 can comprise one or more regions (e.g., 34, 54, 58) corresponding to a portion of body 18 configured to be disposed under one or more of one or more metatarsal heads, a hallux, and a calcaneus bone. For example, a first region 34 of body 18 having a first one or more of cavities 22 may be disposed between a first end 38 of the body and a second end 42 of the body. In the depicted embodiment, first region 34 extends from a first side 46 of the body to a second side 50 of the body. For example, first region 34 of body 18 is closer to first end 38 of body 18 than second end 42 of the body. In this embodiment, when apparatus 10 is use, first region 34 can be configured to be disposed under a plantar surface 30 of one or more metatarsal heads of a foot 14.

A second region 54 of body 18 having a second one or more of cavities 22 may be disposed between first region 34 and first end 38 of the body. More specifically, as shown, second region 54 extends from first region 34 toward first end 38. In the embodiment shown, second region is closer to first side 46 of body 18 than second side 50 of the body. For example, second region 54 is disposed along first side 46. In this embodiment, when apparatus 10 is in use, second region 54 may be configured to be disposed under a plantar surface 30 of a hallux of a foot 14.

A third region 58 of body 18 having a third one or more of cavities 22 may be disposed at second end 42 of the body. As shown, third region 58 can extend from first side 46 to second side 50 at second end 42 of body 18. In this embodiment, when apparatus 10 is in use, third region 58 may be configured to be disposed under a plantar surface 30 of a calcaneus bone of a foot 14.

Apparatus 10 may include a second body 62 that is substantially similar to body 18, with the primary exception that the second body is configured to be positioned above a dorsal surface 66 of a foot 14 to help redistribute shear stresses which normally act on the plantar surface of the foot. In this embodiment, stress can be calculated by dividing a magnitude of mechanical force by a surface area on which the mechanical force acts. Typically, a dorsal surface 66 of a foot 14 bears minimal pressure and/or shear stress within a shoe 26. Second body 62, however, can be configured to reduce shear stress magnitudes on a plantar surface 30 of a foot 14. For example, fluid in second body 62 can help reduce shear stresses that occur when mechanical forces are applied to a plantar surface 30 of the foot (e.g., during heel contact and push-off phases). In this way and others, second body 62 can also help with blood perfusion to a foot 14, which may be compromised in diabetic patients.

Cavities 22 can be prefabricated with standard sizes and/or cross-sectional shapes. For example, one or more of cavities 22 can be triangular, rectangular, square, or otherwise polygonal, circular, elliptical, or otherwise rounded.

Referring to FIGS. 4A-4D and FIGS. 5A and 5B, shown therein and designated by the reference numeral 18a is an exemplary embodiment of a body, which may be suitable for use in some embodiments of the present apparatuses 10. In this embodiment, each of cavities 22 can be pressurized between a first position (e.g., FIGS. 4A, 4C, and 5A), in which the cavity has a first pressure, and a second position (e.g., FIGS. 4B, 4D, and 5B), in which the cavity has a second pressure that is greater than the first pressure. Body 18a includes an elastomeric material configured to deform when one or more of cavities 22 moves between the first and second positions.

In the depicted embodiment, two or more adjacent cavities 22 can share a sidewall 70 such that an inflation surface 74 of the adjacent cavities is connected. In this way and others, body 18a provides a smooth transition between a cavity 22 that is in the first position and a cavity 22 that is in the second position. Sidewall 70 and/or inflation surface 74 may each have a thickness between approximately any two of the following: 0.1, 0.5, 1, 2, 3, 4, 5, 6, 7, 8, 9, and 10 millimeters (mm).

Referring now to FIGS. 6A-6D and FIGS. 7-9, shown therein and designated by the reference numeral 18b is an exemplary embodiment of a body, which may be suitable for use in some embodiments of the present apparatuses 10. In this embodiment, each of cavities 22 can be pressurized between a first position (e.g., FIGS. 6A and 6C), in which the cavity has a first pressure, and a second position (e.g., FIGS. 6B and 6D), in which the cavity has a second pressure that is greater than the first pressure. In the depicted embodiment, body 18b can include a (e.g., substantially flat) substrate 78 configured to be coupled to one or more of cavities 22. More specifically, body 18b can include a plurality of protrusions 82 extending from substrate 78 to define one or more of cavities 22. In this embodiment, one or more protrusions 82 can include an elastomeric material configured to deform when a respective cavity 22 moves between the first and second positions.

As shown, each cavity 22 is defined by a sidewall 70 and an inflation surface 74. In this embodiment, adjacent cavities 22 do not share a sidewall 70, and thus, adjacent inflation surfaces 74 are disconnected. In the depicted embodiment, one of protrusions 82 is separated from an adjacent one of the protrusions by a distance between approximately any two of the following: 0.5, 1, 1.5, 2, 2.5, 3, 3.5, 4, 4.5, 5, 5.5, and 6 mm.

In the depicted embodiment, apparatus 10 includes a flexible substrate 86 configured to distribute pressure (e.g., from weight of the patient) among one or more of cavities 22 and to maximize contact with a plantar surface 30 of a foot 14. As shown, substrate 86 is configured to be disposed over a plurality of cavities 22 such that the substrate matches the contours of the cavity. Substrate 86 may comprise a soft and/or flexible material, such as, for example, rubber and/or foam. Substrate 86 may be filled with a fluid (e.g., gel, air, water, oil, and/or the like). As shown, substrate 86 can be substantially flat such that the substrate is in contact with only a plantar surface 30 of a foot 14. In other embodiments, a substrate (e.g., 86) may be curved such that the substrate contacts medial and/or lateral sides of a foot (e.g., 14). In this way and others, substrate 86 can conform to a plantar surface 30 of a foot 14 regardless of pressure in cavities 22.

Figure 11:
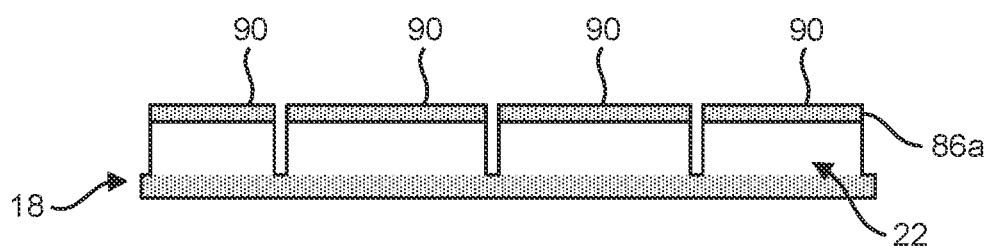
FIG. 11 is a side view of a second embodiment of a substrate that may be suitable for use in some embodiments of the present apparatuses.

Referring now to FIG. 11, shown therein and designated by the reference numeral 86a is a second embodiment of the present flexible substrates. Substrate 86a is substantially similar to substrate 86, with the primary exception that substrate 86a includes a plurality of flexible substrate segments 90, each of which is configured to be disposed over a respective cavity 22 of body 18. By dividing substrate 86a into segments 90, the substrate allows for more selective pressure modulation. For example, when one of cavities 22 is pressurized, material of substrate 86a that is adjacent to the pressurized cavity (e.g., one or more segments 90 on adjacent cavities 22) is not constrained to deflect upwards as it would be if the substrate was continuous (e.g., similar to substrate 86).

Figure 12:
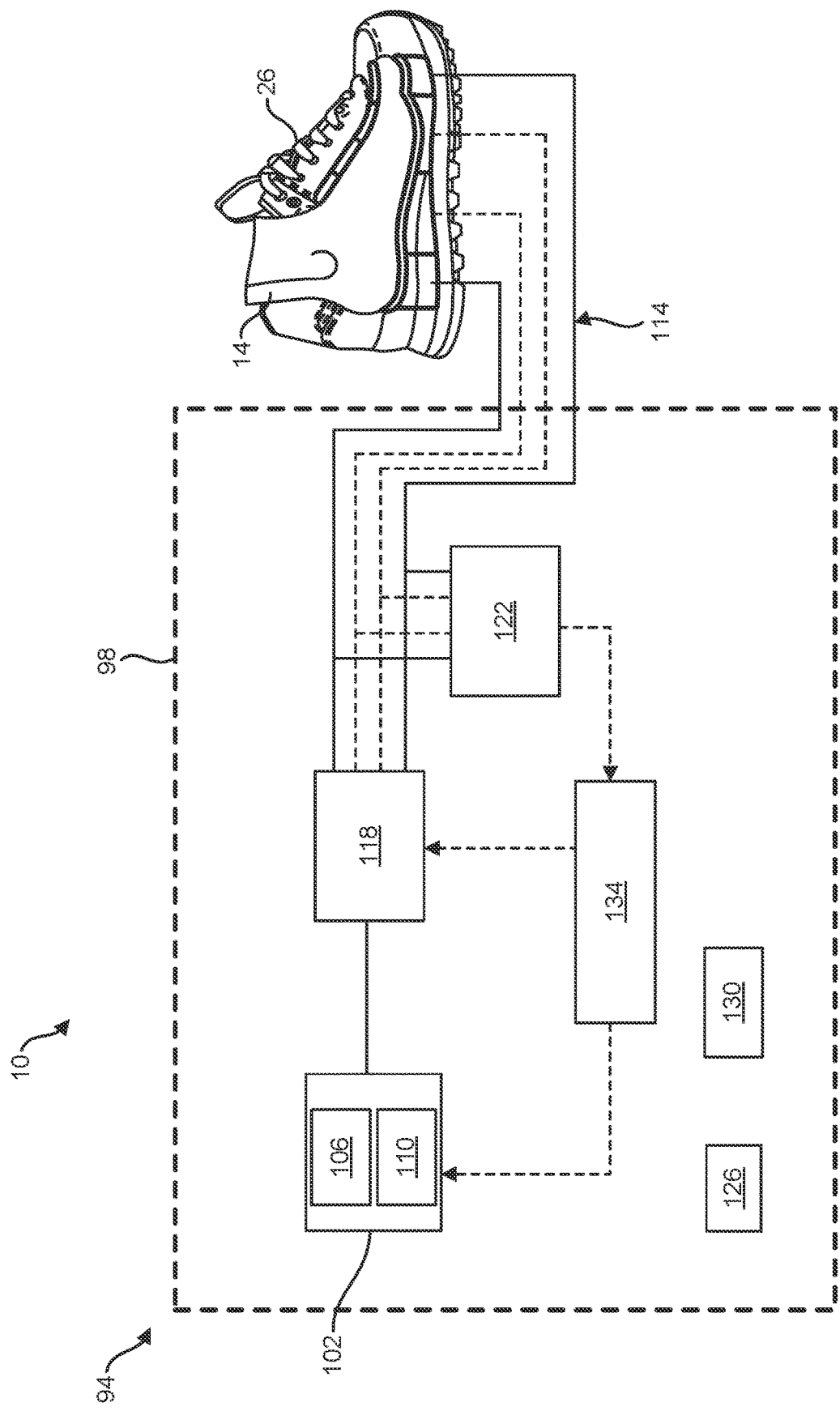
FIG. 12 is a schematic of a first embodiment of a control unit that may be suitable for use in some embodiments of the present apparatuses.

Referring additionally to FIG. 12, apparatus 10 includes a control unit 94 configured to control modulation of cavities 22. Control unit 94 comprises a housing 98 configured to hold one or more components of the control unit. Housing 98 is configured to be coupled to an article of a patient's clothing (e.g., on an outer surface of a shoe 26, a belt buckle, a belt loop, and/or the like) and/or carried by the patient (e.g., in a container, bag, and/or the like).

Control unit 94 comprises a fluid source 102 configured to control pressure within one or more cavities 22. For example, fluid source 102 includes a pump 106 and a fluid reservoir 110 that is coupled to body 18 via one or more conduits 114 (e.g., pneumatic, hydraulic, electronic, and/or the like) such that the fluid source is in communication with one or more of cavities 22 via the conduits. In some embodiments, a fluid source (e.g., 102) can comprise any suitable combination of a pump (e.g., 106), a pressure regulator, a valve, a secondary fluid reservoir, and/or a pressurized air canister coupled to one or more components of a control unit (e.g., 94). For example, in some embodiments, a fluid source (e.g., 102) comprises a pump (e.g., 106) and a pressure regulator, a pump (e.g., 106) and a valve, a pump (e.g., 106) and a secondary fluid reservoir, and/or a pressurized air canister. Control unit 94 includes one or more valves 118 (e.g., a ball valve and/or the like that can comprise any suitable configuration, such as, for example, two-port two-way (2P2W), 2P3W, 2P4W, 3P4W) configured to selectively control fluid flow between one or more of cavities 22 and fluid source 102.

In this embodiment, control unit 94 comprises one or more sensors 122 configured to capture data indicative of a pressure in one or more of the cavities. For example, at least one sensor 122 may include a pressure sensor (e.g., a piezoelectric pressure sensor, strain gauge, and/or the like).

Control unit 94 may include one or more wireless communication components 126 configured to communicate with a peripheral apparatus (e.g., a computer, a mobile phone, a tablet, and/or the like) such that a patient and/or clinician can control apparatus 10 using the peripheral apparatus. For example, wireless communication components 126 can be in electrical and/or fluid communication with and/or communicate data from sensors 122, valves 118, and/or fluid source 102 through processor 134 to a peripheral device. Control unit 94 may be powered by one or more batteries 130. For example, battery 130 is configured to provide electrical power to one or more components of control unit 94 (e.g., pump 106, valves 118, sensors 122, components 126, and/or a processor (e.g., 134)).

Control unit 94 may include a processor 134 configured to control fluid source 102 to, while pressure in a first one or more of cavities 22 remains substantially constant: (a) increase pressure of a second one or more of the cavities; (b) after a predetermined amount of time, decrease pressure of the second one or more of the cavities; and (c) increase pressure of a third one or more of the cavities.

For example, to inflate one or more cavities 22, pump 106 moves fluid from fluid reservoir 110 to pressurize the one or more cavities. When the desired pressure is reached, pump 106 is switched off and one or more of valves 118 corresponding to one or more of cavities 22 is closed to seal the cavity(ies). In embodiments where fluid in one or more of cavities 22 comprises a gas (e.g., air), the cavity may be deflated by, for example, opening one or more of valves 118 to atmosphere pressure to bleed off pressure in the cavity until a desired pressure is reached. In other embodiments, to deflate one or more cavities (e.g., 22), fluid in the cavity may be moved to a reservoir (e.g., 110) via one or more conduits (e.g., 114). One or more of sensors 122 can be used to monitor the pressure of one or more of cavities 22 during inflation and/or deflation and can provide the pressure data to processor 134. Processor 134 can control a duration of time of the inflation and/or deflation, operation of pump 106, opening and/or closing of one or more of valves 118, and ensure the proper level of inflation is achieved in one or more cavities 22 by monitoring internal pressure of the cavities via sensors 122.

Figure 13:
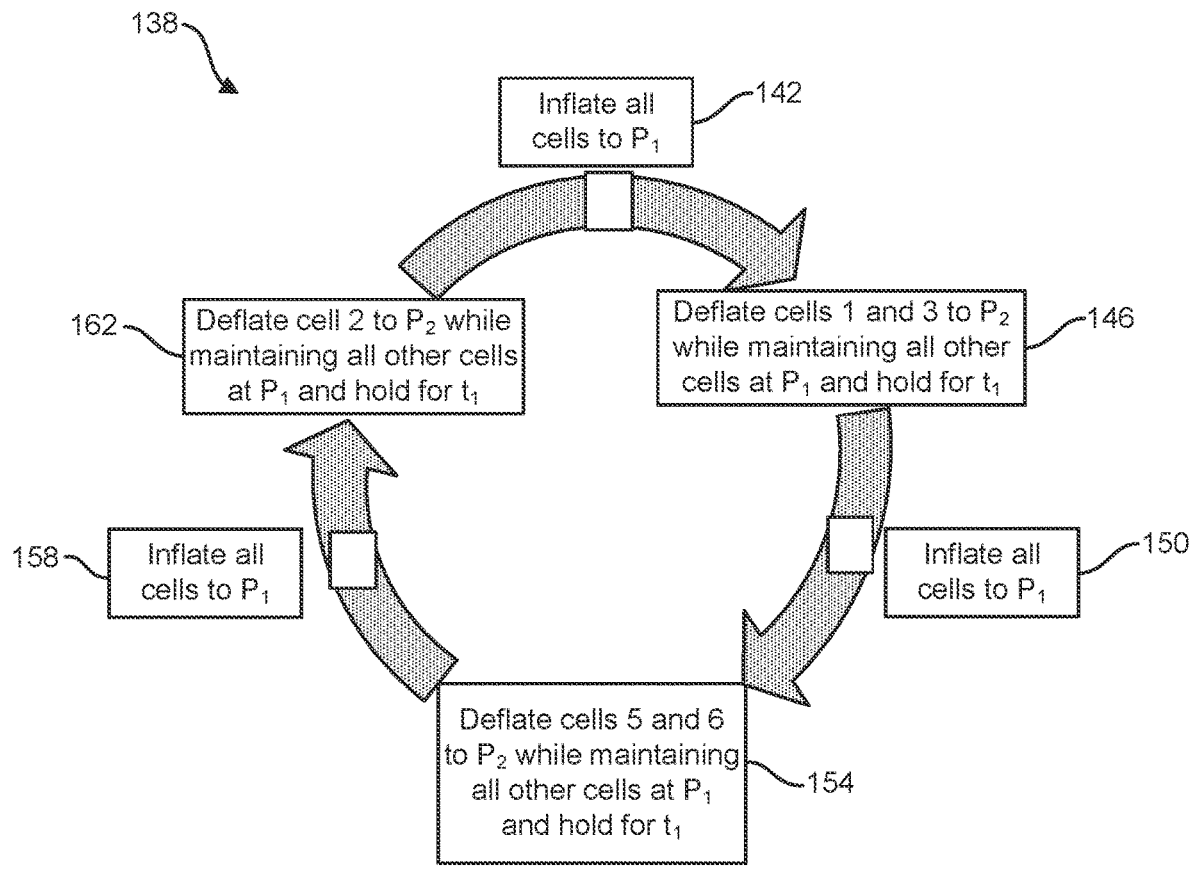
FIG. 13 depicts a conceptual flowchart showing an embodiment of the present methods for actuating some embodiments of the present apparatuses.

Apparatus 10 can be configured to facilitate specifying which cavities 22 are inflated and/or deflated, a duration of time that the cavities are inflated and/or deflated, an internal pressure of the cavities, and/or the like. In this way and others, apparatus 10 selectively cyclically offloads selected regions of a foot 14 so that each region is prevented from being exposed to prolonged excessive mechanical stresses. To illustrate, FIG. 13 depicts an embodiment 138 of the present methods. Method 138 can be implemented, in part or in whole, by processor 134.

At step 142, cavities 22 (e.g., most or all of the cavities) are inflated to a first (e.g., predetermined) pressure. At step 146, while a first one or more of the cavities 22 remain pressurized at the first pressure, a second one or more cavities 22 are deflated to a second (e.g., predetermined) pressure that is less than the first pressure. Thereafter, the pressure of cavities 22, whether at the first pressure or at the second pressure, is held for a (e.g., predetermined) duration of time. At step 150, the second one or more cavities 22 that are pressurized at the second pressure are inflated to be pressurized at the first pressure. At step 154, while the first and second one or more cavities 22 remain pressurized at the first pressure, a third one or more of cavities 22, different from the first and second one or more cavities, is deflated to the second pressure. Thereafter, the pressure of cavities 22, whether at the first pressure or at the second pressure, is held for a predetermined amount of time. At step 158, the third one or more cavities 22 that are pressurized at the second pressure are inflated to be pressurized at the first pressure. At step 162, while the first, second, and third cavities 22 remain pressurized at the first pressure, a fourth one or more of cavities 22, different from the first, second, or third one or more cavities, is deflated to the second pressure. Thereafter, the pressure of cavities 22, whether at the first pressure or at the second pressure, is held for a predetermined amount of time.

In this embodiment, the predetermined amount of time that cavities 22 are held at the first pressure and/or second pressure (e.g., in steps 146, 154, 162) can be the same or different. For example, the predetermined amount of time that cavities 22 are held at the first pressure and/or second pressure can be approximately between any two of: 10 seconds (sec), 15 sec, 30 sec, 45 sec, 1 minute (min), 5 min, 10 min, 15 min, 20, min, 25 min, and 30 min. In some embodiments, pressure in one or more cavities (e.g., 22) can be held substantially constant while all steps (e.g., 142-162) of a method (e.g., 138) are performed (e.g., held substantially constant at a deflated pressure in order to accommodate preexisting foot lesions, such as ulcers and/or the like). For further example, processor 134 may be configured such that all steps (e.g., 142-162) of method 138 are performed at a predetermined frequency, such as, for example, every 5, 10, 15, 20, 25, 30, 45, 60, 75, or 90 min. One or more steps 142-162 of method 138 can be repeated any appropriate number of times. One or more steps 142-162 of method 138 can be performed simultaneously. For example, method 138 can include simultaneously decreasing pressure of at least two of the first, second, and third one or more cavities 22.

In the depicted embodiment, the first pressure and/or the second pressure can be any suitable pressure, such as, for example, between approximately any two of: 0.25, 0.5, 0.75, 1.0, 2.0, 3.0, 4.0, 5.0, 10, 15, 20, 25, 30, 35, 40, 45, and 50 pounds per square inch (psi). In some embodiments, a method (e.g., 138) includes a step where feedback data from a sensor (e.g., 134) is used to determine the duration of time and pressure level at which one or more cavities (e.g., 22) are operated during each step of the method.

In this embodiment, the first one or more cavities 22 of method 138 can be aligned with a plantar surface 30 of one or more metatarsal heads of a foot 14, the second one or more of the cavities of the method can be aligned with the plantar surface of a hallux of the foot, and the third one or more of the cavities of the method can be aligned with the plantar surface of a calcaneus bone of the foot.

EXAMPLES

The present invention will be described in greater detail by way of specific examples. The following examples are offered for illustrative purposes only and are not intended to limit the invention in any manner. Those of skill in the art will readily recognize a variety of noncritical parameters that can be changed or modified to yield essentially the same results.

Figure 14:
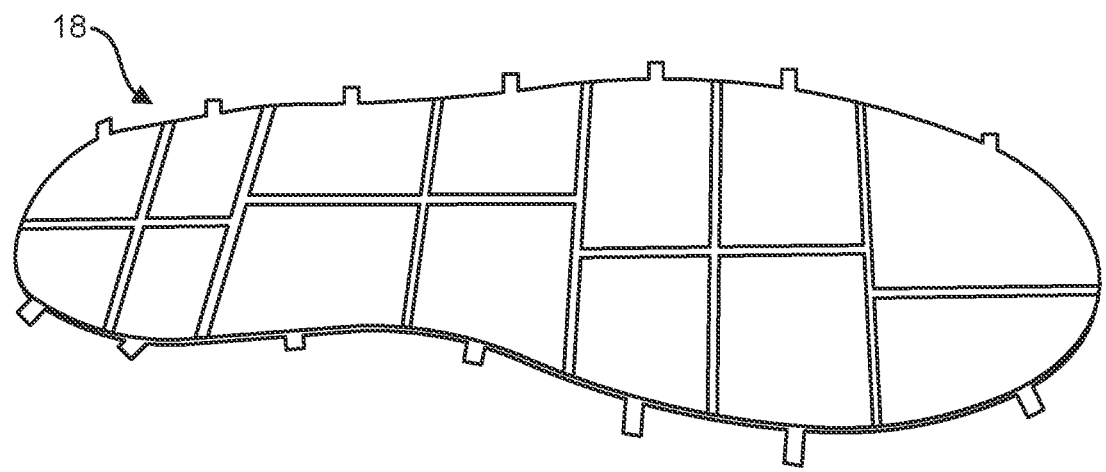
FIGS. 14 and 15 depict a fabricated example of the apparatus of FIG. 1.
Figure 15:
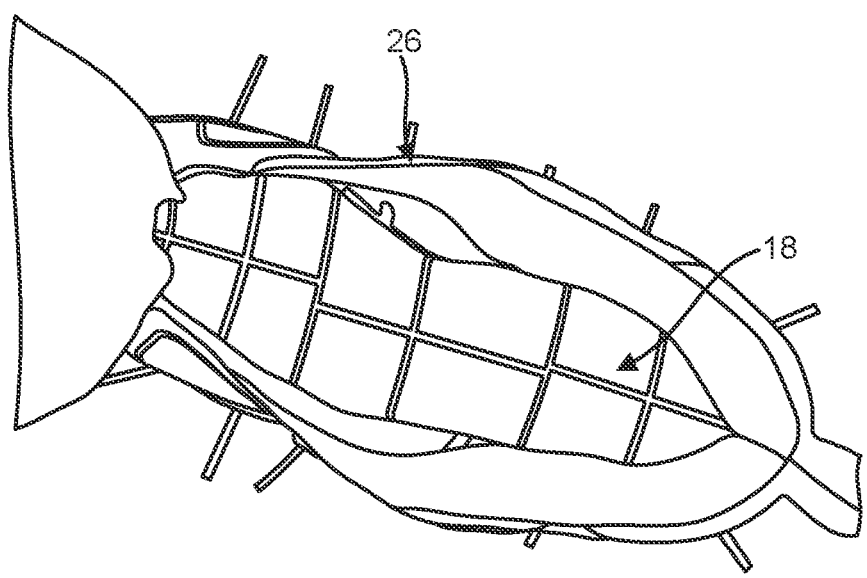

Pressure Mapping and Modulation Using Apparatuses of the Present Disclosure An apparatus (e.g., 10) having a body (e.g., 18) sized for a male shoe size 10.5 was tested to record and analyze pressure mapping and modulation during walking. The body was fabricated using silicone rubbers through a combination of compression molding and over molding techniques. As shown in FIG. 14, the body was integrated with a segmented substrate (e.g., 86a) during the fabrication. Referring additionally to FIG. 15, the body and the substrate were both disposed within a shoe (e.g., 26) for testing.

During testing, the apparatus was worn by an individual exhibiting no symptoms of foot lesions. During testing, an interface pressure sensor was used to verify the pressure mapping and modulation capabilities of the present apparatus. As described herein, interface pressure describes the pressure exerted by the apparatus on the plantar surface of the individual's foot at the interface between the apparatus and the foot.

Figures 16A, 16B:
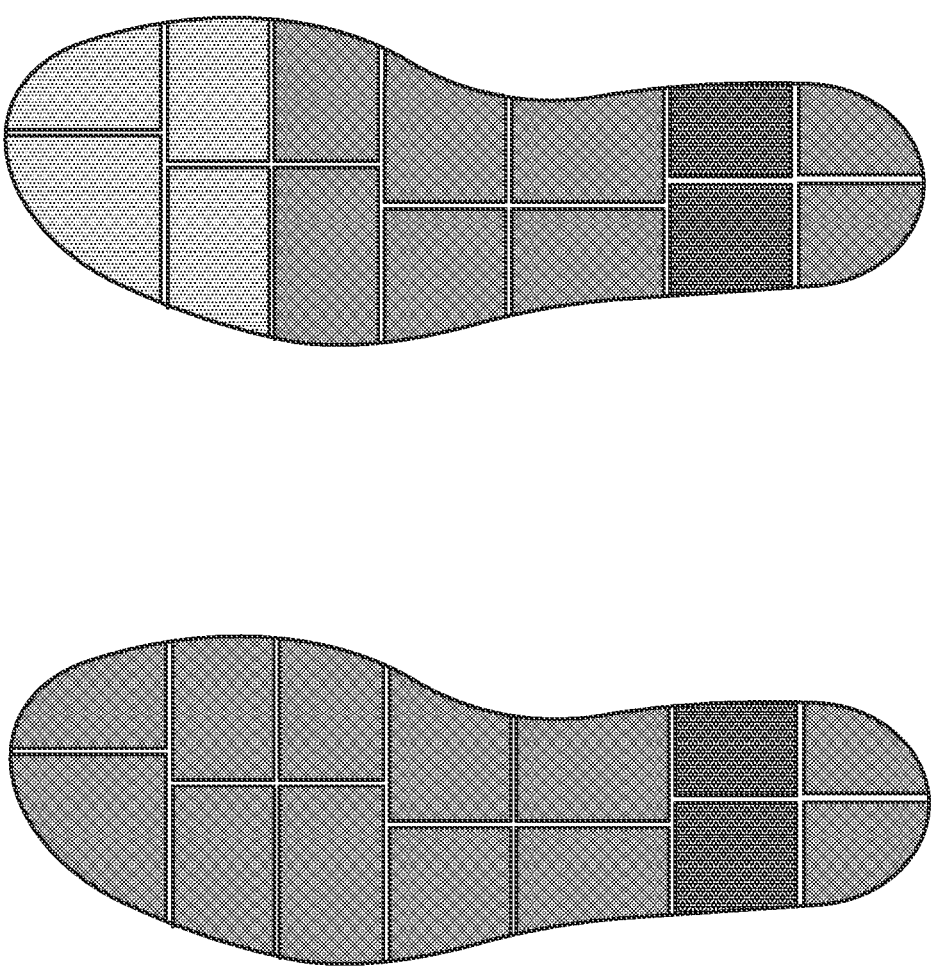

The individual wore the apparatus, which had cavities (e.g., 22) that were pressurized at 14 kPa, in the left shoe and held a standing position (i.e., no walking) for approximately 30 seconds. The plotted internal pressures (e.g., within one or more cavities (e.g., 22)) of the apparatus and interface pressures exerted on the plantar surface of the individual's foot are seen in the FIGS. 16A and 16B, respectively. FIGS. 16A and 16B show that the internal and interface pressures shared a similar pressure distribution. That is, internal pressure within a respective cavity was higher in the same region where the interface pressure was higher and vice versa. Therefore, it was determined that, because internal pressure could be directly correlated to interface pressure, the interface pressure sensor could be eliminated during the actual use of the apparatus. As such, it was determined that varying internal pressure of one or more cavities could be used to modulate the interface pressure exerted on the plantar surface of the individual's foot at least due to the direct relationship between these two measurements.

Next, the pressure mapping and modulation capabilities of the apparatus were tested while the individual walked on a treadmill. The individual wore the apparatus in each shoe to ensure balance during the walking motion. The apparatus in the left shoe had cavities that were pressurized at approximately 6.89 kPa and the apparatus in the right shoe had cavities that were maintained at zero gauge pressure (i.e., non-pressurized). The individual walked at a constant speed of 2 miles per hour on the treadmill for approximately 2 minutes. A control unit (e.g., 94) was able to continuously record the pressure data within each gait cycle with a data sampling rate of 100 Hz.

Figures 17A, 17B, 17C:
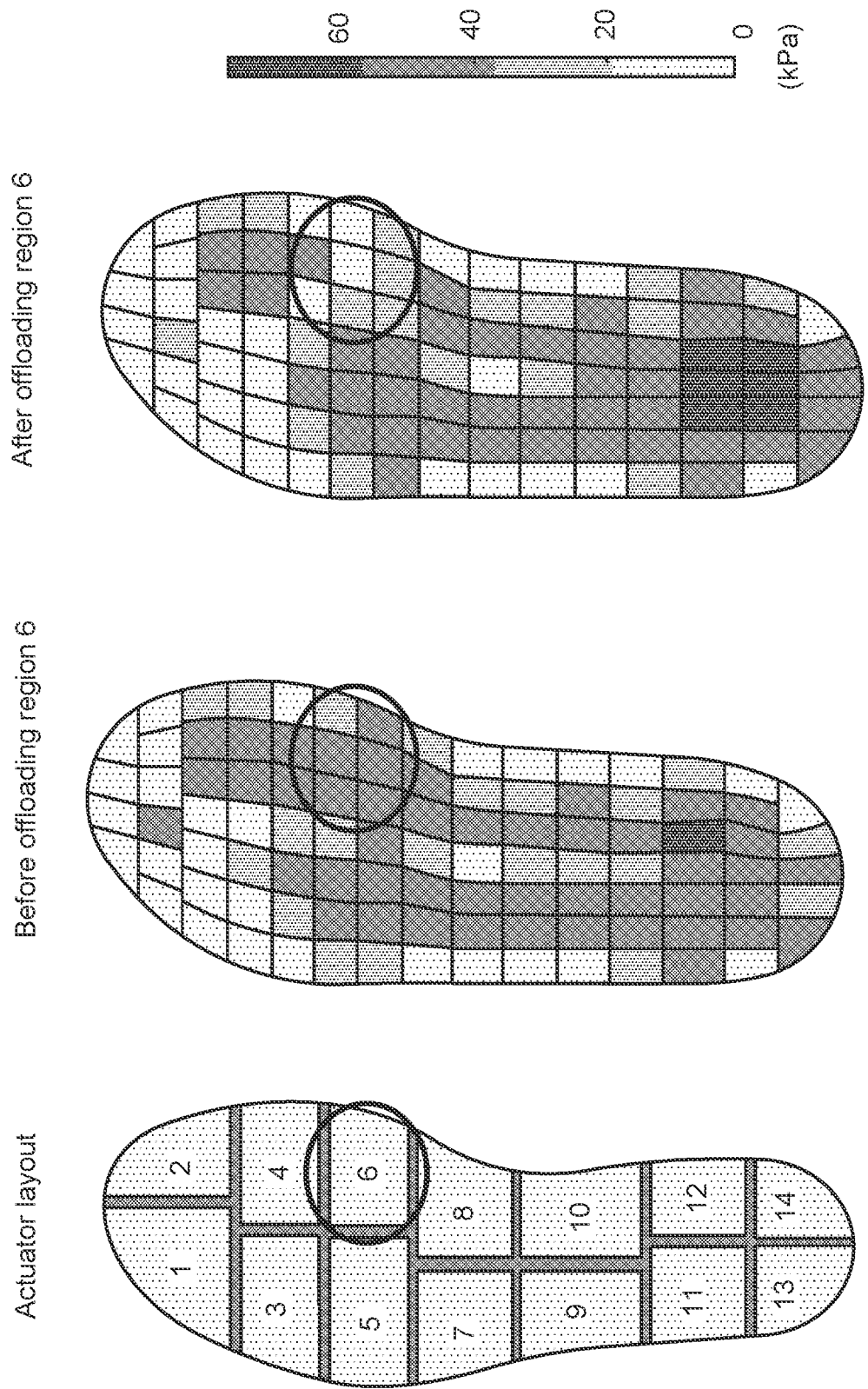

During walking, the internal pressure within the cavities of a region (marked as region 6 in FIG. 17A) of the body was relieved to reduce the interface pressure at the corresponding area of the plantar surface of the individual's foot. As shown in FIG. 17A, region 6 is configured to be aligned with one or more metatarsal heads of the individual's foot. FIG. 17B shows the average interface pressure within the body of the apparatus, before pressure at region 6 was offloaded. FIG. 17C shows the average interface pressure within the body of the apparatus, after pressure at region 6 was offloaded. As a comparison of FIGS. 17A and 17B clearly indicates, the body exhibited a significant pressure reduction in region 6 after reducing the internal pressure within the cavities of region 6 while the individual kept walking. Thus, by modulating the internal pressure within the cavities of the body, the interface pressure between the body and the plantar surface of the individual's foot was also modulated.

Figure 18:
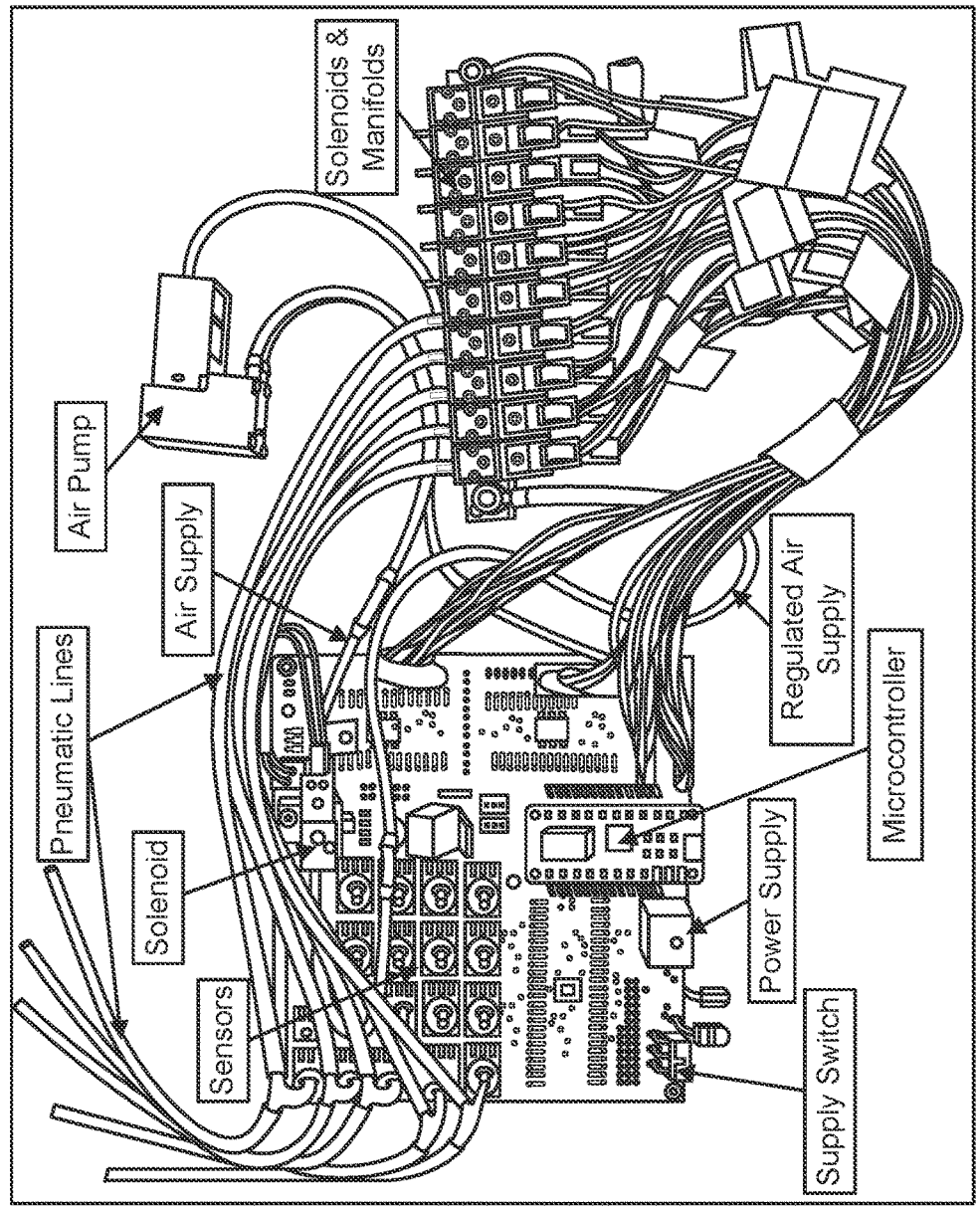
FIG. 18 depicts a fabricated example of the control unit of FIG. 1.

Referring additionally to FIG. 18, shown therein is the control unit used to record pressure data and control pressures within the cavities of the body. As shown in FIG. 18, the control unit included a microcontroller (e.g., 134), an array of sensors (e.g., 122), an array of solenoids mounted on manifolds (e.g., 118), an air pump (e.g., 106) and supply indicators. These components were continuously monitored and controlled by the microcontroller. The array of sensors facilitated the microcontroller in acquiring data indicative of pressure within the cavities of the body. The solenoids and manifold assembly provided a regulated pressure to the cavities.

The sensors acquired data indicative of the pressure within pneumatic lines (e.g., 114) between the cavities and the respective solenoids. For pressure modulation of individual or a group of cavities, the microcontroller controlled the switching of the solenoids based on sensed pressure data and commanded pressure data. As a result, internal pressure within the cavities was increased or decreased to match the commanded pressure data. The commanded pressure data was either provided manually or was determined algorithmically by the microcontroller.

The control unit was operated through a Graphical User Interface (GUI), where a user inputted commands that were processed by the microcontroller. The GUI provided an easier control of the system and allowed the user to perform operations, such as, continuous monitoring and recording of the internal pressure of the cavities, selection of the cavities to be modulated, commanding the selected cavities to a set pressure for pressure offloading and redistribution purposes.

The air supply from the pump was connected to a sensor and an inline solenoid to provide a regulated air supply to the manifolds. The sensor provided feedback regarding the pressure supplied by the air pump and the inline solenoid was switched to control the air supply from the pump to and from the cavities.

Some embodiments of the present methods for actuating an insole apparatus (e.g., 10) having a body (e.g., 18) defining a plurality of cavities (e.g., 22) configured to be coupled to a fluid source (e.g., 102) such that the fluid source can deliver fluid to vary internal pressures of the cavities, wherein the body defines an insole-shaped structure, the method comprises, while pressure in a first one of the cavities remains substantially constant: (1) increasing pressure of a second one of the cavities; (2) after a first predetermined amount of time, decreasing pressure of the second one or more of the cavities; (3) increasing pressure of a third one or more of the cavities; (4) after a second predetermined amount of time, decreasing pressure of the third one or more of the cavities; and (5) increasing pressure of a fourth one or more of the cavities.

In some methods, the second one or more of the cavities (e.g., 22) is aligned with a plantar surface of one or more metatarsal heads of a foot (e.g., 14), the third one or more of the cavities is aligned with the plantar surface of a hallux of the foot; and the fourth one or more of the cavities is aligned with the plantar surface of a calcaneus bone of the foot.

In some methods, the pressure in the first, second, and/or third one of the cavities (e.g., 22) is increased to a value between 0.5 pounds per square inch (psi) and 30 psi, such as, for example, between 0.5 psi and 15 psi.

In some methods, the first predetermined amount of time is between 30 seconds to 30 minutes, and/or the second predetermined amount of time is between 30 seconds to 30 minutes.

In some methods, steps (1)-(5) are controlled by a processor (e.g., 134). In some methods, steps (1)-(5) are repeated. Some methods comprise simultaneously decreasing pressure of at least two of the first, second, and third one or more of the cavities (e.g., 22).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An insole apparatus to distribute pressure and sheer stresses on a foot due caused by mechanical loading due to walking or running comprising:
   a body defining a plurality of cavities configured to be coupled to a fluid source such that the fluid source can deliver fluid to vary internal pressures of the cavities;
   wherein the body defines an insole-shaped structure and the insole apparatus is configured to removably fit within a shoe; and
   a processor configured to control the fluid source to:
   (a) hold pressure in a first one or more of the cavities to be substantially constant;
   (b) increase pressure of a second one or more of the cavities while the pressure in the first one or more of the cavities remains substantially constant;
   (c) after a predetermined amount of time, decrease pressure of the second one or more of the cavities while the pressure in the first one or more of the cavities remains substantially constant; and
   (d) increase pressure of a third one or more of the cavities while the pressure in the first one or more of the cavities remains substantially constant.

2. The insole apparatus of claim 1, wherein the body is configured to be disposed under a patient's foot such that one or more of the cavities is disposed under a plantar surface of at least one portion of the patient's foot selected from the group consisting of: a metatarsal head, a hallux, and a calcaneus bone.

3. The insole apparatus of claim 1, comprising a flexible substrate configured to be disposed over the cavities such that the flexible substrate matches the contours of the plurality of cavities.

4. The insole apparatus of claim 3, where the flexible substrate includes a plurality of flexible substrate segments, each of which is configured to be disposed over a respective cavity.

5. The insole apparatus of claim 3, wherein the body includes a plurality of protrusions extending toward the flexible substrate to define the cavities.

6. The insole apparatus of claim 5, wherein each of the protrusions includes an elastomeric material configured to deform when the internal pressure of the respective cavity is varied.

7. The insole apparatus of claim 1, comprising at least one sensor configured to capture data indicative of a pressure in one or more of the cavities.

8. The insole apparatus of claim 1, wherein:
   a first one or more of the cavities is in a first region of the body extending from a first side of the body to a second side of the body, wherein the first region is closer to a first end of the body than a second end of the body;
   a second one or more of the cavities is in a second region of the body extending from the first region toward the first end and along the first side; and
   a third one or more of the cavities are in a third region of the body extending from the first side to the second side at the second end.

9. The insole apparatus of claim 8, wherein, when in use, the first region is configured to be disposed under a plantar surface of one or more metatarsal heads of a foot, the second region is configured to be disposed under a plantar surface of a hallux of a foot, and the third region is configured to be disposed under a plantar surface of a calcaneus bone of a foot.

10. The insole apparatus of claim 1, comprising a second body defining a plurality of cavities configured to be coupled to the fluid source such that the fluid source can deliver fluid to vary internal pressures of the cavities, wherein, when in use, the second body is configured to be positioned above a dorsal surface of a foot.

11. The insole apparatus of claim 1, wherein at least one cavity of the plurality of cavities includes a valve to atmosphere pressure, and the processor is further configured to open the value to bleed off pressure in the at least one cavity until a desired pressure is reached in the at least one cavity.

12. The insole apparatus of claim 1, wherein the processor within the insole apparatus is further configured to:
   fill the first one or more of the cavities with the fluid before the wearer puts on the shoe; and
   fill the second one or more of the cavities with the fluid after the wearer puts on the shoe.

13. A method for actuating an insole apparatus having a body defining a plurality of cavities configured to be coupled to a fluid source such that the fluid source can deliver fluid to vary internal pressures of the cavities, wherein the body defines an insole-shaped structure and the insole apparatus is configured to removably fit within a shoe of a wearer and to distribute pressure and sheer stresses on a foot due caused by mechanical loading due to walking or running, the method comprising:
   (1) while the wearer is walking or running, holding pressure in a first one or more of the cavities to be substantially constant;
   (2) while the wearer is walking or running, increasing pressure of a second one of the cavities while the pressure in the first one or more of the cavities remains substantially constant;
   (3) while the wearer is walking or running, after a first predetermined amount of time, decreasing pressure of the second one or more of the cavities while the pressure in the first one or more of the cavities remains substantially constant;
   (4) while the wearer is walking or running, increasing pressure of a third one or more of the cavities while the pressure in the first one or more of the cavities remains substantially constant;
   (5) while the wearer is walking or running, after a second predetermined amount of time, decreasing pressure of the third one or more of the cavities while the pressure in the first one or more of the cavities remains substantially constant; and
   (6) while the wearer is walking or running, increasing pressure of a fourth one or more of the cavities, wherein insole apparatus is configured to removably fit within a shoe.

14. The method of claim 13, wherein:
   the second one or more of the cavities is aligned with a plantar surface of one or more metatarsal heads of a foot;
   the third one or more of the cavities is aligned with the plantar surface of a hallux of the foot; and
   the fourth one or more of the cavities is aligned with the plantar surface of a calcaneus bone of the foot.

15. The method of claim 13, wherein steps (1)-(6) are controlled by a processor.

16. The method of claim 13, comprising repeating steps (1)-(6).

17. The method of claim 13, comprising simultaneously decreasing pressure of at least two of the first, second, and third one or more of the cavities while the pressure in the first one or more of the cavities remains substantially constant.

18. A method for actuating an insole apparatus having a body defining a plurality of cavities configured to be coupled to a fluid source such that the fluid source can deliver fluid to vary internal pressures of the cavities, wherein the body defines an insole-shaped structure and the insole apparatus is configured to removably fit within a shoe of a wearer and to distribute pressure and sheer stresses on a foot due caused by mechanical loading due to walking or running, the method comprising:
   (1) while the wearer is walking or running, increasing a first, second, and third one of the cavities to a first pressure;
   (2) while the wearer is walking or running, decreasing pressure of the second one of the cavities to a second pressure while maintaining the first and third one of the cavities at the first pressure;
   (3) while the wearer is walking or running, after a first predetermined amount of time, increasing pressure of the second one of the cavities to the first pressure;
   (4) while the wearer is walking or running, decreasing pressure of the third one of the cavities to the second pressure while maintaining the first and second one of the cavities at the first pressure;
   (5) while the wearer is walking or running, after a second predetermined amount of time, increasing pressure of the third one or more of the cavities to the first pressure; and
   (6) while the wearer is walking or running, decreasing pressure of the first one of the cavities to the second pressure while maintaining the second and third one of the cavities at the first pressure.

19. The method of claim 18, wherein:
   the first one or more of the cavities is aligned with a plantar surface of one or more metatarsal heads of a foot;
   the second one or more of the cavities is aligned with the plantar surface of a hallux of the foot; and
   the third one or more of the cavities is aligned with the plantar surface of a calcaneus bone of the foot.

20. The method of claim 18, comprising simultaneously decreasing pressure of at least two of the first, second, and third one or more of the cavities.

* * * * *